United States Patent
Azar (10) Patent No.: US 9,113,694 B2
(45) Date of Patent: Aug. 25, 2015

(54) METHOD AND SYSTEMS FOR EMPLOYING PIGMENTED CREME-TO-POWDER FOR EYEBROW MAKE-UP APPLICATIONS

(76) Inventor: Donna Azar, Astoria, NY (US)

( * ) Notice: Subject to any disclaimer, the term of this patent is extended or adjusted under 35 U.S.C. 154(b) by 1640 days.

(21) Appl. No.: 12/334,521

(22) Filed: Dec. 15, 2008

(65) Prior Publication Data

US 2010/0147318 A1 Jun. 17, 2010

(51) Int. Cl.
| | |
|---|---|
| *A45D 40/24* | (2006.01) |
| *A45D 8/02* | (2006.01) |
| *A61K 8/02* | (2006.01) |
| *A45D 40/26* | (2006.01) |
| *A46B 5/00* | (2006.01) |
| *A46B 11/00* | (2006.01) |
| *A46B 15/00* | (2006.01) |

(52) U.S. Cl.
CPC .............. *A45D 40/24* (2013.01); *A45D 40/262* (2013.01); *A46B 5/0016* (2013.01); *A46B 11/00* (2013.01); *A46B 15/0091* (2013.01); *A61K 8/02* (2013.01); *A46B 2200/1046* (2013.01)

(58) Field of Classification Search
USPC ......... 132/317, 318, 320, 218, 293–294, 297; 401/17–19, 195, 23, 24, 34; D28/86, D28/77
See application file for complete search history.

(56) References Cited

U.S. PATENT DOCUMENTS

| | | | |
|---|---|---|---|
| 1,356,080 A | 2/1920 | Mason | |
| D145,286 S | 2/1946 | Crane | |
| 2,532,110 A | 11/1950 | Lanz | |
| 3,171,416 A | 3/1965 | Pimentel | |
| 3,592,202 A | 7/1971 | Jones | |
| 3,690,777 A * | 9/1972 | Costa | ............... 401/17 |
| 4,452,262 A | 6/1984 | Jankewitz | |
| 4,602,650 A | 7/1986 | Pipkin | |
| 4,796,647 A | 1/1989 | Gueret | |
| 5,056,179 A | 10/1991 | Capponi | |
| 5,195,546 A | 3/1993 | Cansler | |
| 5,373,940 A | 12/1994 | Hillelson | |
| 5,450,865 A | 9/1995 | Park | |
| D370,088 S * | 5/1996 | Burns | ............ D28/86 |
| 5,881,742 A | 3/1999 | Hunsberger | |
| 5,893,373 A | 4/1999 | Reynolds | |
| 6,471,951 B1 | 10/2002 | Nardolillo | |
| 6,612,764 B2 | 9/2003 | Dumler et al. | |
| 6,623,200 B1 | 9/2003 | Gueret | |
| 6,655,391 B2 * | 12/2003 | Sunago | ......... 132/218 |
| 6,726,900 B2 * | 4/2004 | Scancarella et al. | ............ 424/64 |
| 6,811,770 B2 | 11/2004 | Ferrari | |
| 6,814,084 B2 | 11/2004 | Gueret | |
| 6,866,046 B2 | 3/2005 | Gueret | |
| 7,069,936 B2 | 7/2006 | Gueret | |
| 7,089,946 B2 | 8/2006 | Rousselet | |
| 7,156,105 B2 | 1/2007 | Gueret | |

(Continued)

OTHER PUBLICATIONS

PCT, International Search Report for PCT/US2009/067952, Feb. 23, 2010.

*Primary Examiner* — Robyn Doan (57) ABSTRACT

The instant application provides methods and systems for applying color to eyebrows and skin at locations where an eyebrow should be. A crème-to-powder formulation is used to apply the color. The crème-to-powder formulation includes a crème-to-powder base and pigmentation to provide a final color suitable for application as eyebrow makeup. A liquid sealant may be used to seal in the color once applied. Various kits are disclosed that include a crème-to-powder formulation and applicators.

19 Claims, 11 Drawing Sheets

(56) References Cited

U.S. PATENT DOCUMENTS

| | | |
|---|---|---|
| 7,337,929 B2 | 3/2008 | Winckels |
| 7,344,327 B2 | 3/2008 | Gueret |
| 7,350,525 B2 | 4/2008 | Delage |
| 7,350,997 B2 | 4/2008 | Rousselet |
| 7,357,588 B2 | 4/2008 | Liard |
| 7,377,296 B2 | 5/2008 | Gueret |
| 7,377,711 B2 | 5/2008 | Byun |
| 7,381,003 B1 | 6/2008 | Chang |
| 7,384,208 B2 | 6/2008 | Bouix |
| 7,416,357 B2 | 8/2008 | Thiebaut |
| 7,416,360 B2 | 8/2008 | Tajima |
| 7,419,321 B2 | 9/2008 | Tereschouk |
| 7,422,389 B2 | 9/2008 | Abergel |
| 7,553,100 B2 * | 6/2009 | Muhr-Sweeney .............. 401/23 |
| 2003/0152410 A1 | 8/2003 | Huang |
| 2005/0142084 A1 | 6/2005 | Ganguly et al. |
| 2007/0020205 A1 | 1/2007 | Blin et al. |
| 2008/0102047 A1 | 5/2008 | Appel et al. |

\* cited by examiner

METHOD AND SYSTEMS FOR EMPLOYING PIGMENTED CRÈME-TO-POWDER FOR EYEBROW MAKE-UP APPLICATIONS

FIELD OF THE INVENTION

The present invention relates generally to eyebrow makeup and related methods of application. More particularly, the present invention discloses a system and related method that employ a pigmented crème-to-powder formulation for application to eyebrows.

BACKGROUND OF THE INVENTION

The texturing and highlighting of eyebrows is an old art, and many products are available on the market to provide for fuller, more textured eyebrows. Each of these products, however, suffers from frustrating defects.

A first application method and system employs brushes that are used to apply pigmented powder and wax. In many kits, the brushes are short in the handle (approximately 2 inches in length) and thus do not allow for the proper placement of color; that is, such short brushes are not user-friendly. A brush should ideally be long enough to place color and to measure angles for proper placement of the color. If the brush is of adequate length the brush may be used as a measuring tool for the application of color, being used to mark three points that may then be filled in to make the brow: straight up against the nose for the inside corner of brow, than towards the peak diagonal to the iris of the eye, and than a little further to the corner of the eye. The brushes that are long enough usually are not hard enough to properly push the pigment into the brow or onto bare skin. This leaves the user with an unattractive, improper application.

Secondly, the brushes are usually sold in kit form containing a powder and wax duo. The powder is used as a pigment to color the eyebrow or skin, while the wax is used as a sealant for the powder. The consumer is expected to use the same brush for applying both the powder color and the wax for setting the color on bare skin, brow hair or both for holding the brow hair in place. This dual use of the brush, however, creates problems. The wax builds up on the brush leaving it slippery and clumpy, and thus unsuitable for proper application of color. The wax itself may leave a clumpy and unattractive result to the brow hair. Additionally, on bare skin the wax may leave a shiny, ruddy application.

Other kits exist that employ pencils. These pencils need to be sharpened, which can be tedious for the user. They are either wax-based or powder-based. The wax-based pencils need to be pushed hard onto the skin for a suitable application of pigment. The pigment in wax-based pencils typically does not adhere well to the skin, which creates a drawn on, shiny, ruddy (reddish) application. As a result the user is left with an unattractive, unnatural result. Powder-based pencils are softer, but the user still has to draw the application on. This method does not allow for hair-like strokes or pushing pigment into the skin. Thus, pencils are not suitable for building texture.

A third kit and related method of applying color to the brow is in the form of a mascara-type wand that has a formula that is pumped from a tube. The formula can either have pigment or be clear. The user brushes the brow hair to place color, or clear formula to set the brow. This application usually dries and gets clumpy, and moreover tends to flake when dry. It can thus appear like dandruff in the eyebrow. Also, people with sparse or bare brows cannot use this application because the brush heads are usually bristly and can cause irritation to bare skin.

Yet another type of application comprises a tube containing a pigment that has a handle with a sponge-like applicator. This application is messy and does not adhere to the brow hair or skin properly.

Users of such makeup products have long been frustrated by these drawbacks, and yet despite this long-felt need in the field no one has yet arrived at an eyebrow makeup application method and system that does not suffer from at least one of the above-mention drawbacks. Accordingly, there is an immediate need for an improved system and method for applying makeup to eyebrows.

SUMMARY OF THE INVENTION

One aspect provides a method for applying eyebrow makeup to the brow hair or skin of a user. While in a crème state, a crème-to-powder formulation is applied to an eyebrow, or to the skin at a location corresponding to the eyebrow. The crème-to-powder formulation is pigmented to have a color that is suitable for application as eyebrow makeup. In preferred embodiments, a sealant is then placed over the crème-to-powder formulation. The sealant is preferably a liquid sealant. In various embodiments, the crème-to-powder formulation comprises a crème-to-powder base and one or more pigments to provide the crème-to-powder formulation a color suitable for application as eyebrow makeup. Preferably, the crème-to-powder formulation is applied only to the eyebrow, or to skin at a location corresponding to the eyebrow.

In another aspect, various kits are disclosed for performing the above embodiment methods. Preferred embodiment kits include a first casing comprising a first reservoir and a first dispensing end fluidly connected to the first reservoir. A crème-to-powder formulation is disposed within the first reservoir, and a first applicator head is provided to permit a user to apply the crème-to-powder formulation.

In a specific embodiment, the first applicator head is attached to an end of the casing, and the kit further comprises a wand for removably closing the first dispensing end, in which the wand terminates in a second applicator head.

In various other embodiments, the casing further comprises a second reservoir and a second dispensing end fluidly connected to the second reservoir. A liquid sealant is disposed within the second reservoir. In one such embodiment, a first dispensing system is provided for dispensing the crème-to-powder formulation from the first reservoir to the first dispensing end, and a second dispensing system is further provided for dispensing the liquid sealant from the second reservoir to the second dispensing end. In this specific embodiment, a second applicator head is fluidly connected to the second dispensing end, and the first applicator head is fluidly connected to the first dispensing end. In an alternative embodiment, a first dispensing system is provided for dispensing the crème-to-powder formulation from the first reservoir to the first dispensing end, and a wand is provided for removably closing the second dispensing end. In this specific embodiment, the wand includes a second applicator head, and the first applicator head is fluidly connected to the first dispensing end. In yet another variation, a first wand is provided for removably closing the first dispensing end, in which the first applicator head is attached to the first wand, and a second wand is provided for removably closing the second dispensing end, in which the second wand terminates in a second applicator head.

In another embodiment kit, a first casing includes a first dispensing system for dispensing aliquots of the crème-to-powder formulation from the first dispensing end. This embodiment kit also includes a second casing with a second reservoir for holding a liquid sealant, and a second dispensing end connected fluidly connected to the second reservoir. A wand terminating in a second applicator head is used to close the second dispensing end, and the first applicator head is fluidly connected to the first dispensing end.

In yet another embodiment kit, the first casing includes a first dispensing system for dispensing aliquots of the crème-to-powder formulation from the first dispensing end. Similarly, a second casing having a second dispensing system dispenses aliquots of a liquid sealant from a dispensing end of the second casing.

In yet another embodiment, first and second casings respectively hold a crème-to-powder formulation and a liquid sealant. A dual-ended wand removably closes the dispensing ends of each casing. The first applicator head is connected to one end of the dual-ended wand, and a second applicator head is connected to the other end of the dual-ended wand.

DETAILED DESCRIPTION

One aspect of the invention provides a method for applying color to a brow using a crème-to-powder formulation to apply the color, in which the crème-to-powder formulation is preferably pigmented to have a color suitable for application to eyebrows. Crème-to-powder makeup is well-known in the industry, and is typically used for applications to the skin on the face as a foundation application. Such applications prepare the skin surface for other products to be applied on top of the foundation provided by the crème-to-powder product, and these other products provide the final color; for example, a pigmented blush for the ball of the cheeks or a pigmented bronzing powder for illumination to the face. The crème-to-powder product applies like a crème, but upon exposure to air dries to leave a suitably pigmented powdery residue. Heretofore, no crème-to-powder product has been pigmented for application to the eyebrow; all such products have instead been exclusively limited to skin surfaces and not eyebrows. It is believed that even the darkest crème-to-powder products on the market are unsuitable for application to eyebrows. There does not currently exist, and to date no one has contemplated or appreciated the advantages of, a crème-to-powder formulation having a color that is suitable for application to the eyebrows.

The present invention employs any suitable crème-to-powder base, such as is used, for example and without limitation, in Yves Saint Laurent #5 "Teint Singulier Voile Fondant Poudre Sheer Powdercreme Veil." Of course, any other suitable crème-to-powder base may be used. For example, the crème-to-powder bases disclosed in the following United States Patents may be suitable: U.S. Pat. No. 6,267,970 to Matesevac et al., entitled "Cream cosmetic base with powdery feel"; U.S. Pat. No. 5,871,756 to Jeffcoat et al., entitled "Cosmetics containing thermally-inhibited starches"; and U.S. Pat. No. 5,338,535 to Berndt, entitled "Non-aqueous liquid powder"; the contents of all of which are incorporated herein by reference. In its original form, the crème-to-powder base may be white, or may be pigmented. However, the present invention further employs one or more pigments within the crème-to-powder base to provide a crème-to-powder formulation having a color that is preferably suitable for application to eyebrows as eyebrow makeup. The pigment is preferably mixed evenly into the crème-to-powder base to create an embodiment crème-to-powder formulation. Embodiment crème-to-powder formulations may have colors identical to those colors used in the prior art for eyebrow makeup. Any suitable pigment may be used to obtain this coloration. Simply by way of example and without limitation, an embodiment crème-to-powder formulation may employ as the crème-to-powder base crème-to-powder as found in the above-indicated Yves Saint Laurent product, or any other suitable crème-to-powder base, and as a pigment into this crème-to-powder base may be mixed pigmented powders, such as powders marketed as eye shadows or powders for application to the eyebrows. The color and amount of pigment to add into the crème-to-powder base to create an embodiment crème-to-powder formulation is up to the user or manufacturer to achieve the desired brow color. Hence, in the following, a crème-to-powder formulation indicates a makeup product having a crème-to-powder base and a sufficient amount and color of pigmentation mixed into the crème-to-powder base to create a formulation having a final color that is preferably suitable for application to eyebrows as eyebrow makeup.

While in a crème state, the crème-to-powder base may have any suitable viscosity. In preferred embodiments, the crème-to-powder formulation has a viscosity from about 1,000 centipoise to about 10,000,000 centipoise; more preferably from about 3,000 centipoise to about 5,000,000 centipoise; more preferably still from about 150,000 centipoise to about 2,000,000 centipoise; more preferably still from about 250,000 centipoise to about 1,000,000 centipoise. Once dry, however, the crème-to-powder formulation is in a powder state.

In preferred embodiment crème-to-powder formulations, three to four shades may be offered for eyebrows, such as for blonde heads, red heads, light brown hair, and brunettes (dark brown to black brown); dark brown and black brown usually use the same color. Pantone® is widely used in industry to provide a standard for the selection and indication of color. The Pantone® matching system (PMS) employs a number to broadly indicate a particular color. In various embodiments, colors indicated by the following PMS numbers may be used as the final color of a crème-to-powder formulation, preferably when in the powder state: 134, 1345, 138, 1385, 139, 1395, 140, 1405, 145, 148, 153, 1535, 154, 1545, 155, 160, 1605, 161, 1615, 1817, 400, 401, 402, 403, 404, 405, 406, 407, 408, 409, 410, 411, 412, 420, 421, 422, 423, 424, 425, 426, 451, 452, 490, 712, 713, 714, 715, 716, 717, 718, 719, 720, 721, 722, 723, 724, 725, 726, 727, 728, 729, 730, 731, 732. In particularly preferred embodiments, the crème-to-powder formulation may be pigmented so that it has a color indicated by the following PMS values, preferably when in the powder state: 1345, 1355, 1385, 1395, 140, 1405, 146, 153, 154, 160, 400, 401, 402, 406, 1817, 420, 422, 451, 452, 490, 712, 719, 721, 727, 729, 732. However, it will be appreciated that other colors may be used for an embodiment crème-to-powder formulation. Generally, any color that the end-user or manufacturer feels may be desirable for application as eyebrow makeup may be used in an embodiment crème-to-powder formulation.

Figure 1:
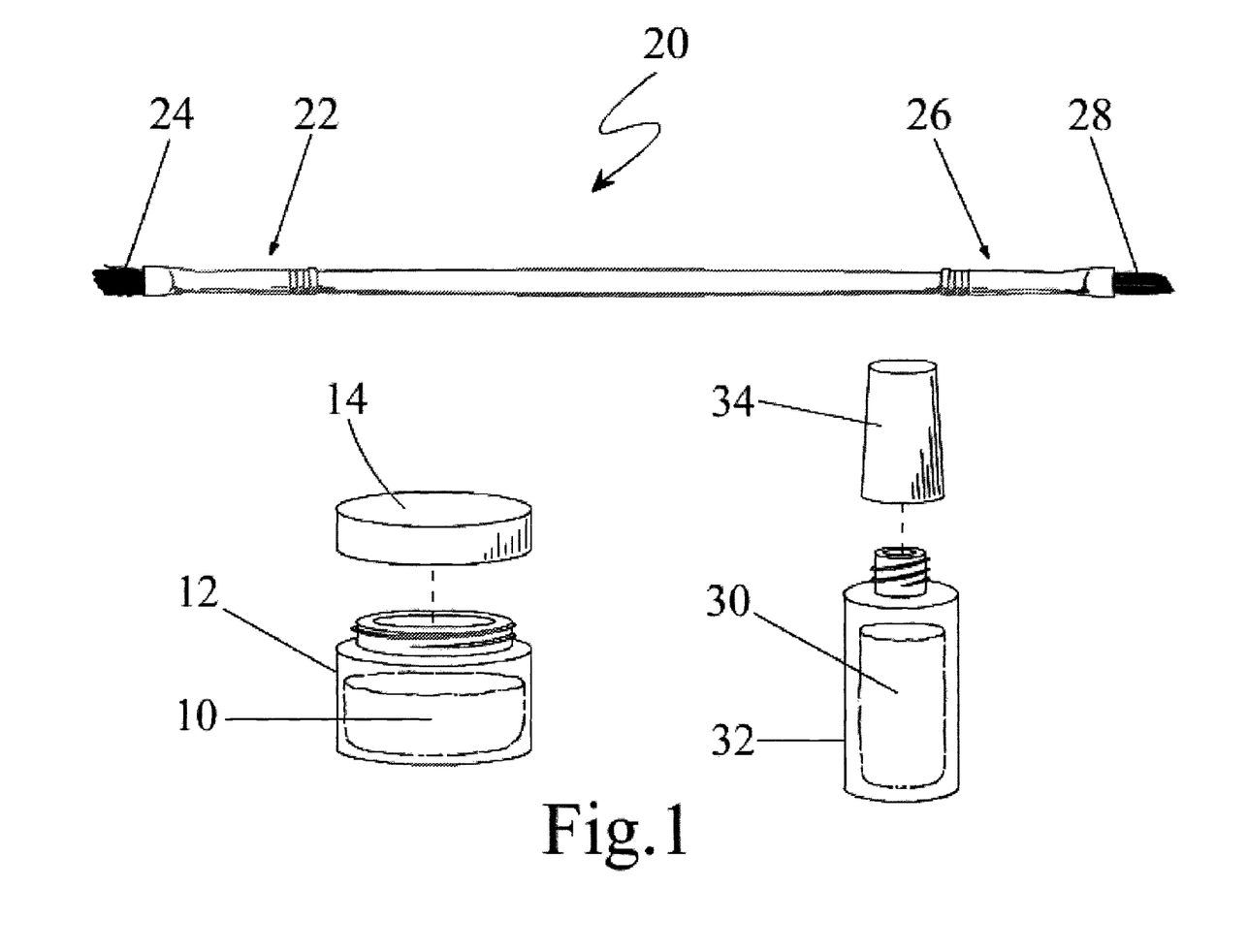
FIG. 1 shows a first system for an embodiment makeup application method.

One embodiment eyebrow makeup application method is described with reference to FIG. 1. A crème-to-powder formulation 10 is stored in a casing that provides a reservoir for holding the crème-to-powder formulation, such as a simple container 12. Container 12 may preferably be sealed when the crème-to-powder formulation 10 is not needed, as exposure to air can cause the formulation 10 to dry out from a crème state to a powder state. The suitably-pigmented crème-to-powder formulation 10 is preferably used in combination with a two-sided applicator 20, although any type of applicator may be used, of course, such as two, single-sided applicators, or even a single, single-sided applicator. For purposes of the following, an applicator is any device that a user may employ to apply the crème-to-powder formulation, to apply a sealant or both. An applicator will include an applicator head, which is that portion of the applicator that contacts the user to apply the crème-to-powder formulation or the sealant. In this and the following embodiments, preferred embodiment applicator heads 24, 28 employ brushes. However, it will be appreciated that other types of applicator heads may be employed, such as foam-like or sponge-like wedges, mascara-like wands, felt tips, or the like. With respect, then, to preferred embodiments, a first end 22 of the applicator 20 has a first brush head 24 that is preferably on a slight angle and tufted. The first brush head 24 can be made from any suitable material, synthetic or natural, such as animal hair. A second end 26 has a second brush head 28 with a slightly larger angle and that is soft in texture. The second brush head 28 can also be made from any suitable material, synthetic or natural, such as animal hair. The second brush head 28 is preferably more soft, flexible or both than the first brush head 24. The applicator 20 is preferably at least 6 inches long, as this allows for stippling and pushing to build color properly into the brow.

A small amount of the crème-to-powder formulation 10, while in the crème state, is placed onto the first, tufted, brush head 24, such as by dipping the first brush head 24 into the container 12. Those of reasonable skill in the art will understand that typically in cosmetic applications less is more. Hence, the user ideally should use just enough of the crème-to-powder formulation 10 to cover the tip of the brush 24. The crème-to-powder formulation 10 is then applied to the eyebrow to visually enhance the eyebrow. The crème-to-powder formulation 10 may also be easily applied to bare skin where, for example, there is no eyebrow but the appearance of an eyebrow is desired, or where the eyebrow is sparse.

By way of example, using the first brush head 24, a first dot or marker of color is placed at the inside corner of the eye eyebrow, by way of the pigmented crème-to-powder formulation 10 present on the first brush head 24. A second dot or marker of color at the peak of the brow is then made, which is at a position diagonal to the iris of the eye. A third dot or marker of color at the tale end of the brow is then made, which may be measured from the corner of the eye. For each of these marking positions, the length of the brush 20 makes it suitable for use as a ruler or straight edge. The user may then begin stippling color into or onto the brow hair or bare skin, using additional amounts of the crème-to-powder formulation 10 as required, working and building up to the peak and than down to the tail end of the brow, the dots or markers serving as guides. As the user applies the crème-to-powder formulation 10 it dries from the original crème state into a powder state. When in powder state, the crème-to-powder formulation 10 allows for depth and fullness to be achieved, with gaps of hair or bare brows having a natural, soft matte appearance; while in a crème state, the crème-to-power formulation 10 is smoothly and easily applied with great control. The crème-to-powder formulation 10 applies easily to bare skin, unlike, for example, wax-based products or pure powder products, and yet also builds easily into the brow hair, unlike powder-based products. Despite the long-felt need in the field for such advantages, no method heretofore appreciated or enjoyed these characteristics of a crème-to-powder formulation 10 for eyebrow applications.

The second brush head 28 of the applicator 20 may then be used to blend and create more refinement in the tail end of the brow if needed. Once application of the brow color, as provided by the crème-to-powder formulation 10, is accomplished, the user may then dip the second brush head 28 into a liquid eyebrow sealant 30 and brush the sealant 30 over the brow. Any suitable liquid sealant 30 may be used, such as sealants commonly available on the market. The sealant 30 locks in the color provided by the crème-to-powder formulation 10, rendering it sweat-proof and smudge-proof. The sealant 30 preferably dries to a matte finish and helps to hold the brow hairs in place. On bare skin, such as may be found for users with no or sparse brows, the sealant 30 will not remove the pigment provided by the crème-to-powder formulation 10 and allows for a natural application of color.

The sealant 30 may be any eyebrow sealant as obtained, for example, from any distributor or wholesaler, such as from private label cosmetic products. Simply by way of example, eyebrow sealant from Brushes by Karen Mineola, N.Y., may be used. The sealant 30 is preferably in liquid form and acts as a barrier to place over bare skin of the brow bone or on top of sparse to full eyebrow hair. When applied with a suitable applicator head, the sealant 30 glides easily over bare skin and sparse to full brow hair. The sealant 30 acts as a vehicle to lock in color/pigment as provided by the formulation 10, rendering the final application sweat-proof and smudge-proof. Application of the sealant 30 is thus beneficial for users who are, for example, active in sports, as it will prevent the eyebrow makeup from smudging or looking ruddy. The sealant 30 may be a day-to-night application and so won't come off until washed off with a cleanser and water. Sealant 30 also helps to set brow hairs in place, making them appear tidier. It is also particularly beneficial for women with no or sparse brows. Preferred embodiments of the sealant 30 won't remove the formulation 10 placed on the bare skin of the brow area, and as the sealant 30 dries to a matte finish it allows for a more natural application of color/pigment. Preferred embodiments of the sealant 30 are also fast drying.

Figure 2:
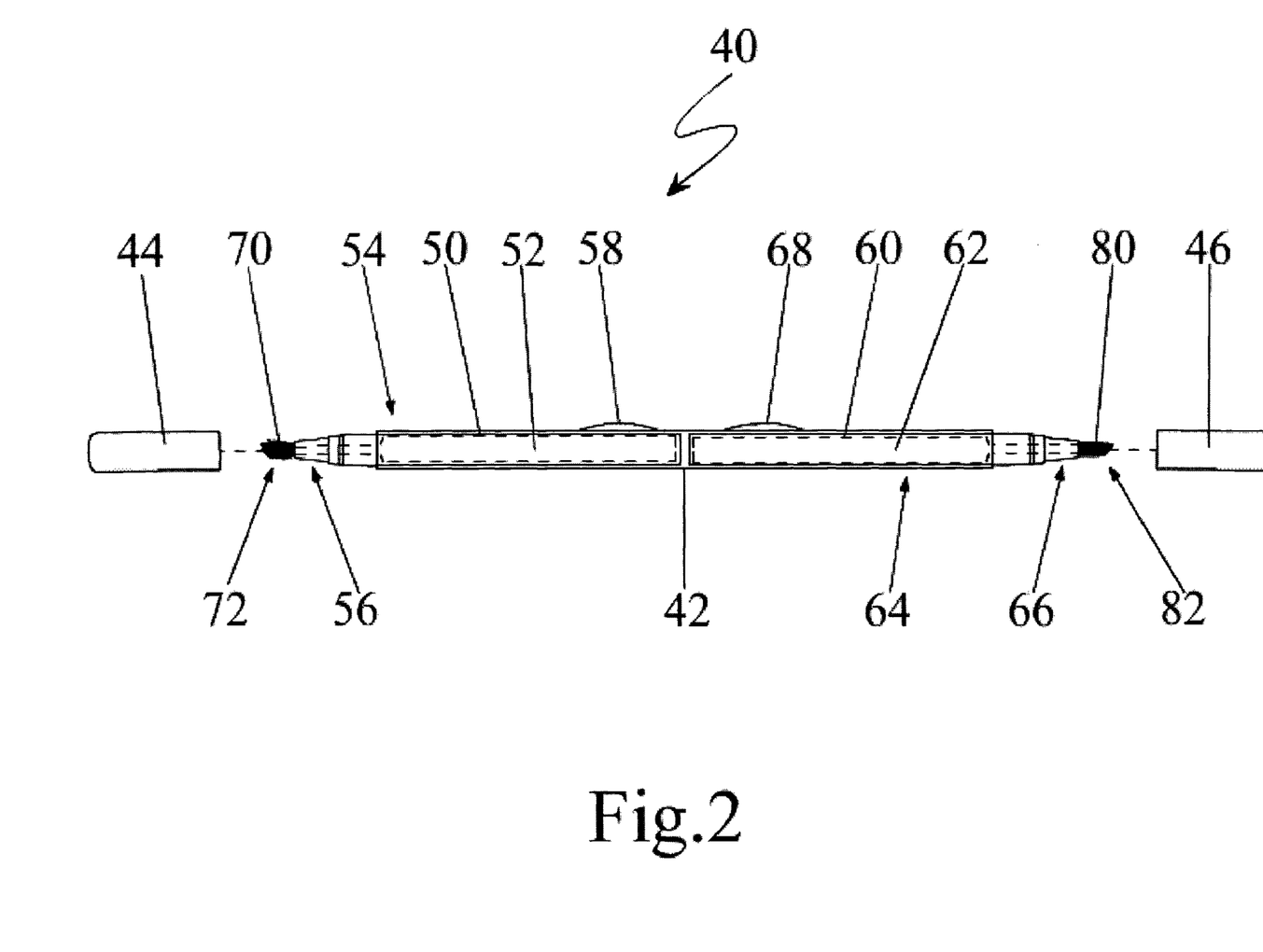
FIG. 2 shows a second system for an embodiment makeup application method.

A first embodiment eyebrow color applicator 40 is shown in FIG. 2. The applicator 40 comprises a casing 42 that preferably measures at least 6 inches in length, although shorter lengths are certainly possible. An internal region or regions of the casing 42 are used to hold or provide a first reservoir 50 and a second reservoir 60. The first reservoir 50 is used to hold an embodiment crème-to-powder formulation 52, while the second reservoir 60 is used to hold eyebrow sealant 62. The sealant 62 is preferably a liquid that, when dry, is sweat-proof and smudge-proof, as described earlier. Any suitable sealant 62, such as those currently available on the market, may be used. The size and diameter of the casing 42 are a design choice that may be determined by the manufacturer. Factors for consideration include, for example, the amount of product 52, 62 to be held in their respective reservoirs 50, 60.

A first end 54 of the casing 42 has a first dispensing end 56 that is fluidly connected to the first reservoir 50 and that dispenses aliquots of the crème-to-powder formulation 52 in response to activation of a first dispensing system 58, which may be activated by the user. As used herein, an aliquot may be an amount deemed by, for example, a manufacturer, to be an ideal amount of material to be dispensed for application in accordance with an embodiment method. This amount may be, for example, experimentally determined, and the dispensing systems 58, 68 may then be configured to respectively dispense suitable amounts of product 52, 62. By pressing upon a button, for example, the dispensing system 58 may cause an aliquot of crème-to-powder formulation 52 to exit from the first dispensing end 56. Alternatively, the dispensing system 58 may comprises a dial that rotates or clicks through a predetermined angle to dispense an aliquot of the crème-to-powder formulation 52 from the first dispensing end 56. Makeup dispensing systems are well-known in the art, and any suitable dispensing system 58 may be used. The dispensing system 58 preferably keeps the crème-to-powder formulation 52 in a suitably sealed environment to prevent drying out of the crème-to-powder formulation 52 while in the first reservoir 50 over the course of the expected lifetime of the applicator 40, such as a month or more. Simply by way of illustration, dispensing systems 58, 68 may employ mechanisms similar to those found in, for example, the Color Quick Fast Dry Nail Color Pen, by Sally Hansen; Touche Eclat Radiant Touch, by Yves Saint Laurent; Nail Touch-Nail Laquer Pen Brush, by Yves Saint Laurent; French Manicure Kit, also by Yves Saint Laurent; and, for example, U.S. Pat. No. 5,339,841 to Jean-Louis Gueret, entitled "Makeup Device", the contents of which are incorporated herein by reference. However, it will be appreciated that any suitable dispensing system 58, 68 may be used to dispense their respective aliquots of product 52, 62.

The first end 54 of the casing 42 terminates in a first applicator head 70, which is preferably a brush head 70. The first dispensing end 56 is fluidly connected to the first brush head 70. This first brush head 70 is preferably about ¼ of an inch in length and is sufficiently firm to permit stippling. The first brush head 70 preferably terminates in a slightly slanted end 72. This slanted end 72 may be used to push and stipple the crème-to-powder formulation 52 into the eyebrow hair or onto bare skin where brow hair should be. A small amount of the crème-to-powder formulation 52 can be dispensed with each click or activation of the first dispensing system 58, allowing the user to build color as needed. In preferred embodiments, this may be enough formulation 52 to just reach the tip of first brush head 70. The crème-to-powder formulation 52 is easy to apply and becomes more blendable as it dries to a matte finish. The embodiment crème-to-powder formulation 52 also builds density between sparse hairs because as the crème becomes a powder it acts as a filler as well. Moreover, because the crème-to-powder formulation 52 dries into a powder, it does not clump up in the first brush head 70, a benefit that has heretofore not been appreciated in the context of eyebrow applications.

A similar configuration is provided for the other end of the applicator 40. A second end 64 of the second reservoir 60 is fluidly connected to a second dispensing end 66 of the casing 42 that dispenses aliquots of the sealant 62 in response to activation of the second dispensing system 68, which may be activated by the user. Any suitable dispensing system 68 may be used, as previously described in relation to the first dispensing system 58. The dispensing system 68 preferably keeps the sealant 62 in a suitably sealed environment to prevent drying out of the sealant 62 while in the second reservoir 60. Both the first reservoir 50 and the second reservoir 60 are preferably non-reactant with their respective fluids 52, 62.

The second end 64 of the casing 42 terminates in a second applicator head 80, which is preferably a brush head 80. The second dispensing end 66 is fluidly connected to the second brush head 80. This second brush head 80 is preferably about ¼ of an inch in length and is softer than the first brush head 70 to permit blending, finer lines and contouring of color to create, for example, more refinement in the tail end of the brow. The second brush head 80 preferably terminates in a slanted end 82 that has a slant greater than that of the slanted end 72 of the first brush head 70.

Once the brow color as provided by the crème-to-powder formulation 52 has been applied and contoured, by activating the second dispensing system 68 the sealant 62 can be used with the same brush 80 as is used for the contouring and thus easily applied directly over the brow or bare skin where a brow should be. Once the user has completed use of the applicator 40, the user may apply a first cap 44 to cover the first dispensing end 56, and apply a second cap 46 to cover the second dispensing end 66 to respectively protect the dispensing ends 56, 66 and applicator heads 70, 80.

Figure 3:
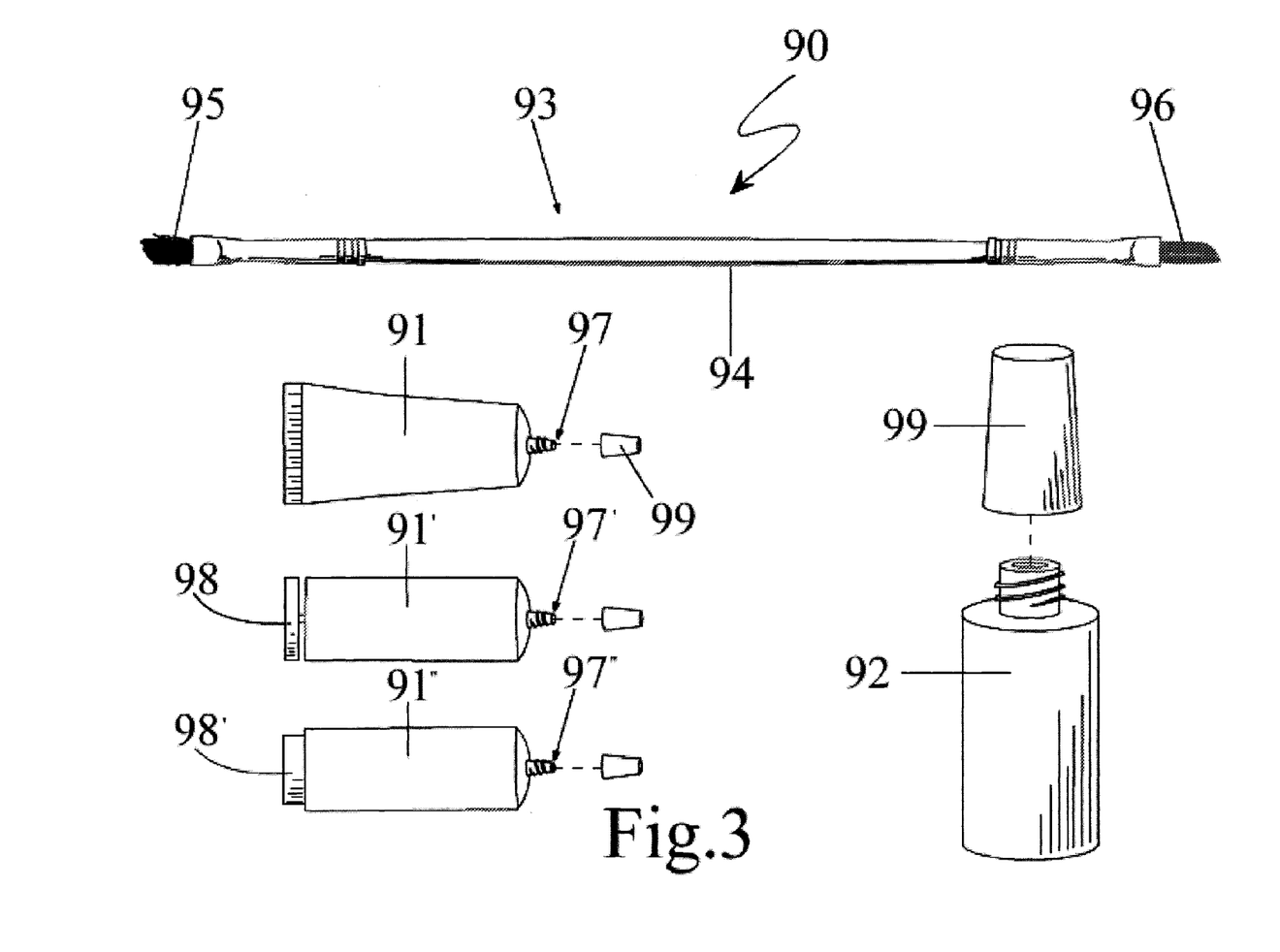
FIG. 3 shows a third system for an embodiment makeup application method.

An embodiment kit 90 is shown in FIG. 3. The kit 90 may include a first casing with a reservoir, such as a container 91, for holding an embodiment crème-to-powder formulation, and a second casing with a reservoir, such as a container 92, for holding a sealant, such as a standard liquid eyebrow sealant. The first container 91 may be, for example, a tube or the like holding approximately 0.5 or 15 ml. of the embodiment crème-to-powder formulation, although other volume amounts are certainly possible. The crème-to-powder formulation may be dispensed, for example, by squeezing on the tube 91 so that aliquots of the crème-to-powder formulation are dispensed from a dispensing end 97 of the container 91. Alternatively, the first container 91', 91" may further include any suitable dispensing system 98, 98', as described above, to dispense aliquots of the crème-to-powder formulation from the dispensing end 97', 97", such as by clicking a button 98' on the container 91", by turning a dial 98 located on the container 91', or any other suitable user-interface means. The kit 90 also includes a two-sided applicator 93, which preferably measures about 7 inches in length. The handle 94 of the applicator 93 may be made from any suitable material, such as wood. One end of the handle 94 has a first applicator head 95, which is preferably a firm brush head that is on a slight angle and tufted, measuring about ¼ of an inch in length. The first brush head 95 may be made from synthetic or natural fibers or bristles, such as animal hair. The first brush head 95 may be used to push and stipple the crème-to-powder formulation into the eyebrow hair or onto bare skin where brow hair should be. Another end of the handle 94 may have a second applicator head 96. This second applicator head 96 is also preferably a brush that may have a slightly longer angle than the first brush head 95, and may also be softer in texture, and thus more flexible, than the first brush head 95. The second brush head 96 may also be made from natural or synthetic fibers or bristles. The second brush head 96 may be used to contour, blend and create more refinement in the tail end of the brow if needed. Once application of the crème-to-powder formulation is accomplished, the user can dip that second brush head 96 into container 92, which may be, for example, plastic or glass and holding approximately 1.5 to 2 oz of liquid eyebrow sealant. The user may then, using the second brush head 96, brush the sealant over the brow to lock in the color, rendering it sweat-proof and smudge-proof. Standard sealants generally dry to a matte finish and help to hold the brow hairs in place. Also, on bare skin (such as for users with no or sparse brows) such sealants do not remove the crème-to-powder formulation and thus allow for a natural application of color.

Figure 4:
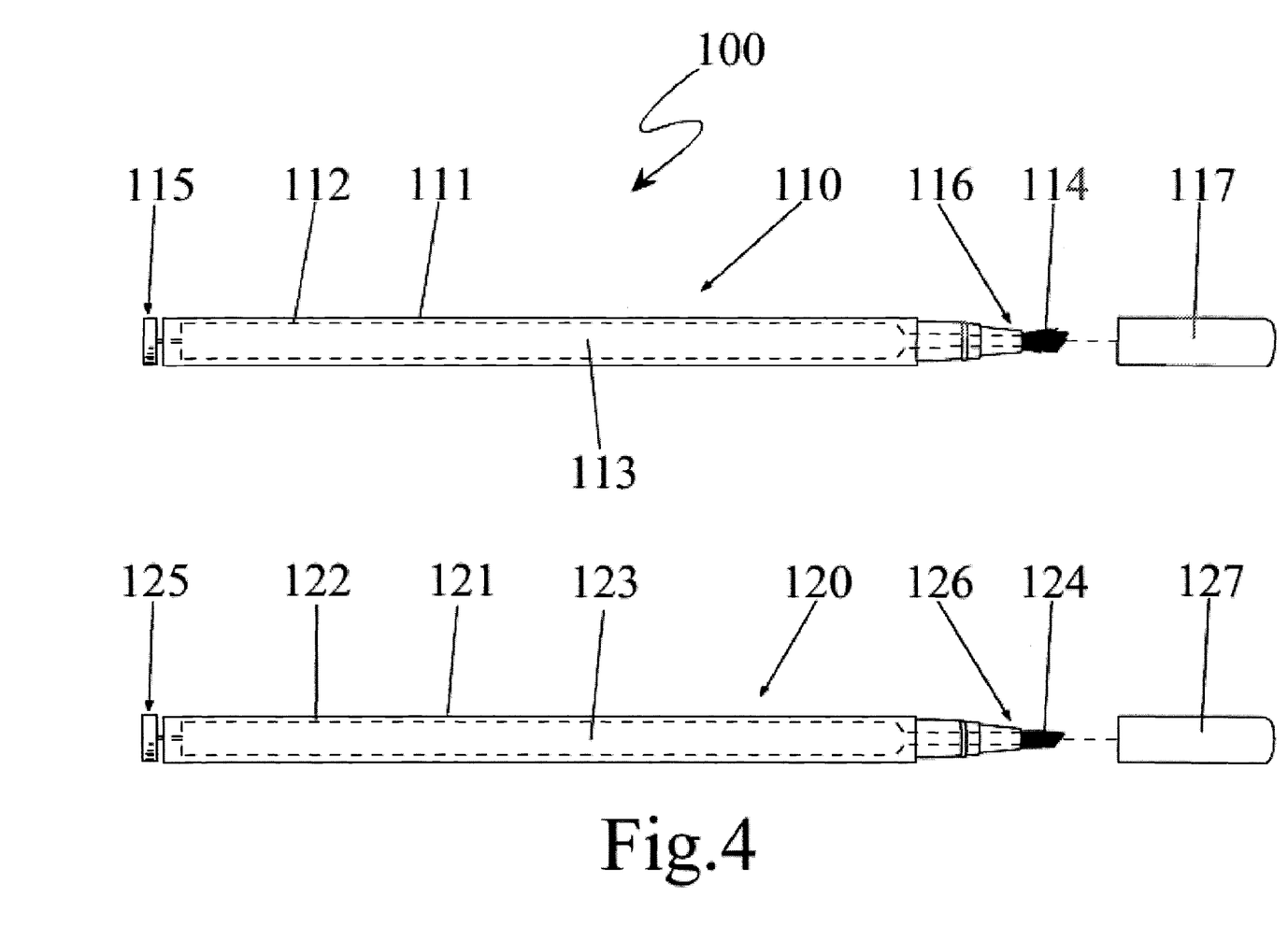
FIG. 4 shows a fourth system for an embodiment makeup application method.

Yet another embodiment kit 100 is shown in FIG. 4. The kit 100 includes a first dispenser 110 and a second dispenser 120. Each dispenser 110, 120 is preferably about seven inches long. Within a casing 111 of the first dispenser 110 is a reservoir 112 which holds an embodiment crème-to-powder formulation 113. One end of the casing 111 has an applicator head 114, which is preferably a brush head and that may be synthetic or natural, and that measures about ¼ of an inch in length. The brush head 114 has a slight angle and is suitably firm and tufted to enable the user to push and stipple the cream-to-powder formulation 113 into eyebrow hair or onto bare skin where brow hair should be. The first dispenser 110 has a dispensing system 115 that may be activated by the user, such as by turning a knob, pressing a button or the like. Any suitable dispensing system 115 may be used. When activated, the dispensing system 115 causes a dispensing end 116 of the casing 111, which is fluidly connected to the reservoir 112, to release an aliquot of the crème-to-powder formulation 113. The brush or other type of applicator head 114 is fluidly connected to this dispensing end 116 so that the aliquot is dispensed onto or into the applicator head 114.

Casing 121 of the second dispenser 120 also has a reservoir 122, which holds a liquid eyebrow sealant 123, such as any commercially available sealant, and which is preferably smudge-proof and sweat-proof. One end of the casing 121 has an applicator head 124, which is preferably a brush head that may be synthetic or natural, and that measures about ¼ of an inch in length. The brush head 124 has a longer angle and is softer and more flexible than the other brush head 114. The brush head 124 may be used for contouring color and for finer lines, such as the tail of the brow. The second dispenser 120 also includes a dispensing system 125 that may be similar to the dispensing system 115. Any suitable dispensing system 125 may be used, however. When activated, the dispensing system 125 causes a dispensing end 126 of the casing 121 to release an aliquot of the sealant 123. The applicator head 124 is fluidly connected to this dispensing end 126 so that the aliquot is dispensed onto or into the applicator head 124.

The reservoirs 112, 122, and the dispensing systems 115, 125 ideally prevent air from entering into the reservoirs 112, 122 to prevent drying out of the respective products 113, 123 within the reservoirs 112, 122 over the expected lifetime of the dispensers 110, 120. In certain embodiments, this may be assisted by way of caps 117, 127 that may be removably installed on the respective dispensing ends 116, 126 to cover the applicator heads 114, 124. In some embodiments, however, depending upon the dispensing system 115, 125 used there may be some nominal drying of product 113, 123 within or near the dispensing ends 116, 126. In certain embodiments the reservoirs 112, 122 may be cartridges or the like that may be removed from their respective casings 111, 121 and replaced. In other embodiments, the casings 111, 121 may be designed so that the respective applicator heads 114, 124 are retractable within the casings 111, 121 in a manner analogous to, for example, lipstick dispensers.

Figure 5:
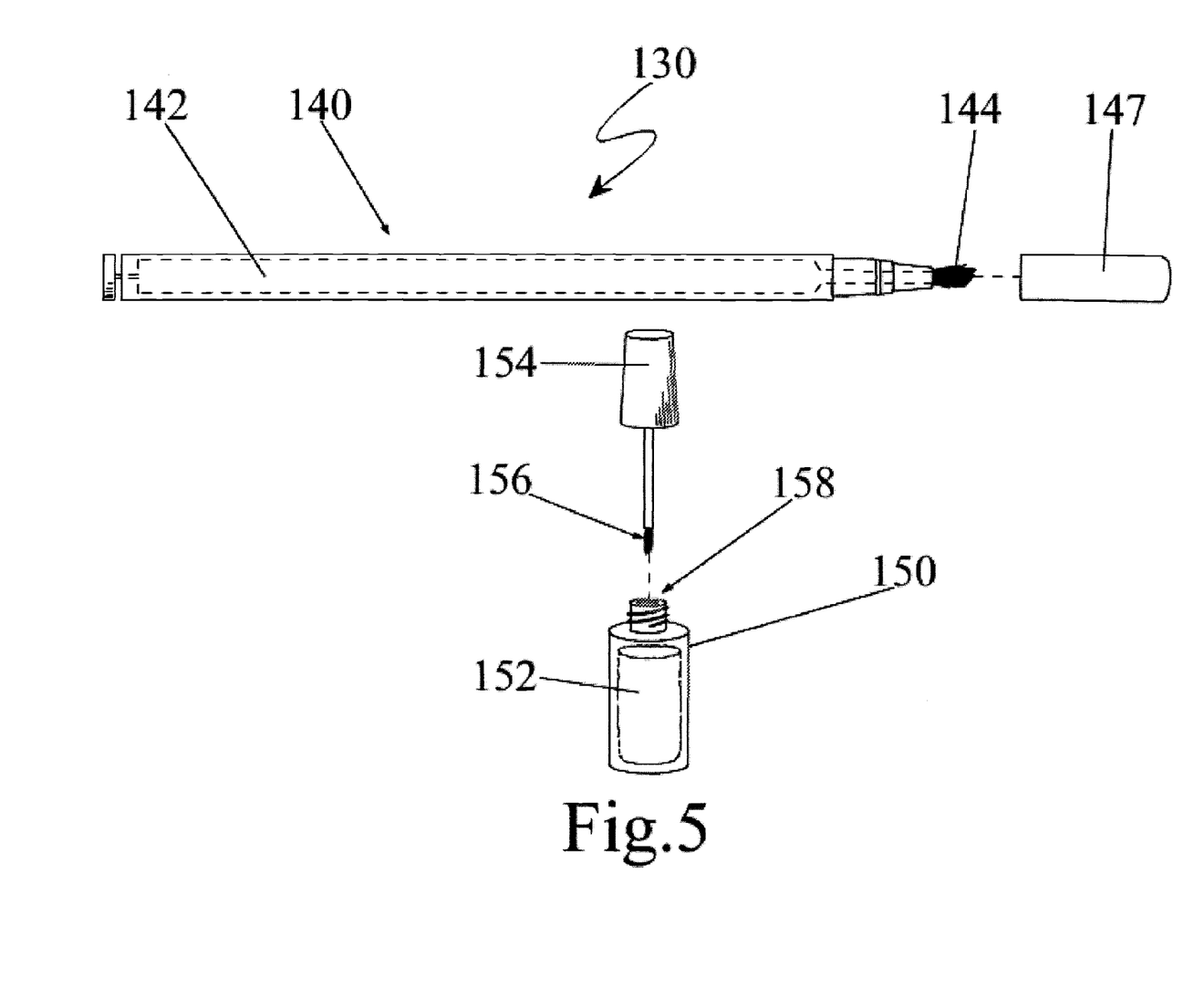
FIG. 5 shows a fifth system for an embodiment makeup application method.

Yet another embodiment kit 130 is shown in FIG. 5. The kit 130 includes a dispenser 140 which may be, for example, similar to the dispenser 110 discussed in relation to FIG. 4, and may be about seven inches in length. The dispenser 140 holds an embodiment crème-to-powder formulation 142 within a reservoir, which may be a replaceable cartridge or permanently installed within the dispenser 140. A dispensing system that may be activated by a user causes an aliquot of the crème-to-powder formulation 142 to be dispensed onto applicator head 144. The applicator head 144 is preferably a firm brush head that has a slight angle and is tufted, measuring approximately ¼ of an inch long, enabling a user to stipple and build color into the brow. In various embodiments, the dispenser 140 may further include a cap 147 or the like for removably covering the applicator head 144, or the applicator head 144 may be retractable within the dispenser 140.

The kit 130 further includes a bottle 150 of liquid sealant 152, which may hold approximately 1.5 to 2 oz of liquid sealant 152, and serves as an applicator for the sealant 152. The bottle 150 provides a casing with a reservoir into which the sealant 152 is disposed, and further includes a wand 154 with an applicator head 156. The applicator head 156 is preferably a brush 156 that may be used to apply the sealant 152 over brow hair or bare skin, and may be softer and more flexible than the brush 144. The sealant 152 is preferably sweat-proof and smudge-proof. The wand 154 acts as a cap and closes the dispensing end 158 in the top of the bottle 150 that provides access to the reservoir of sealant 152.

Figure 6A:
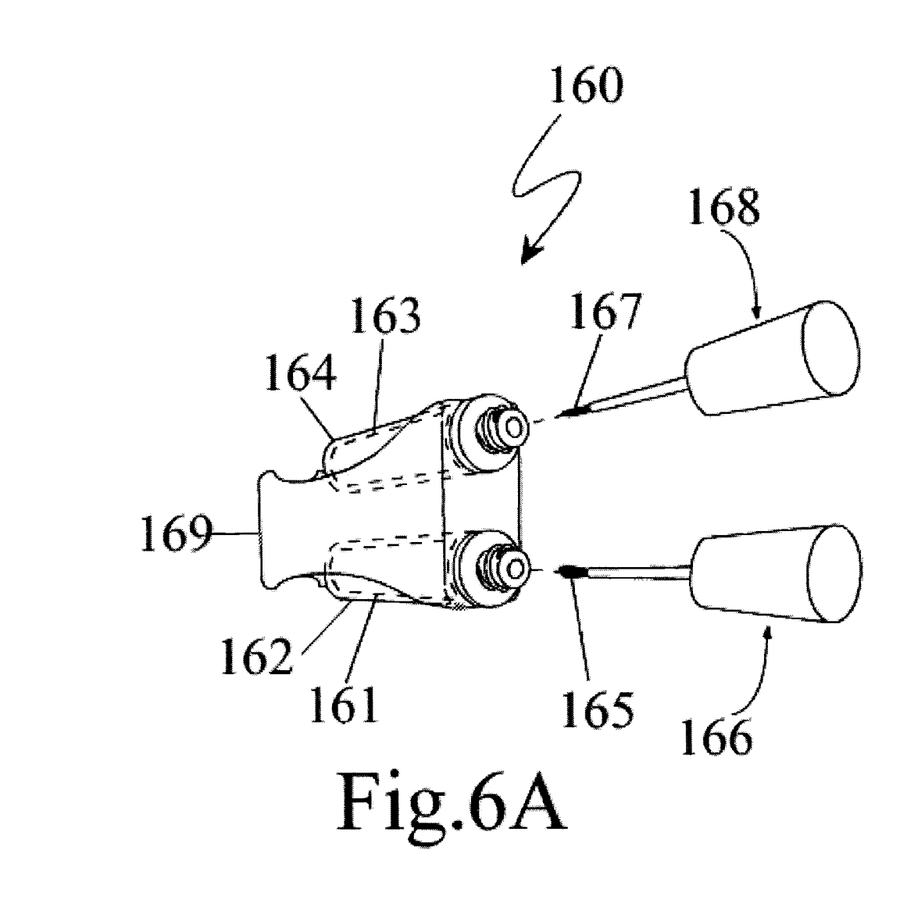
FIGS. 6A-6D show various views of a sixth system for an embodiment makeup application method.
Figure 6B:
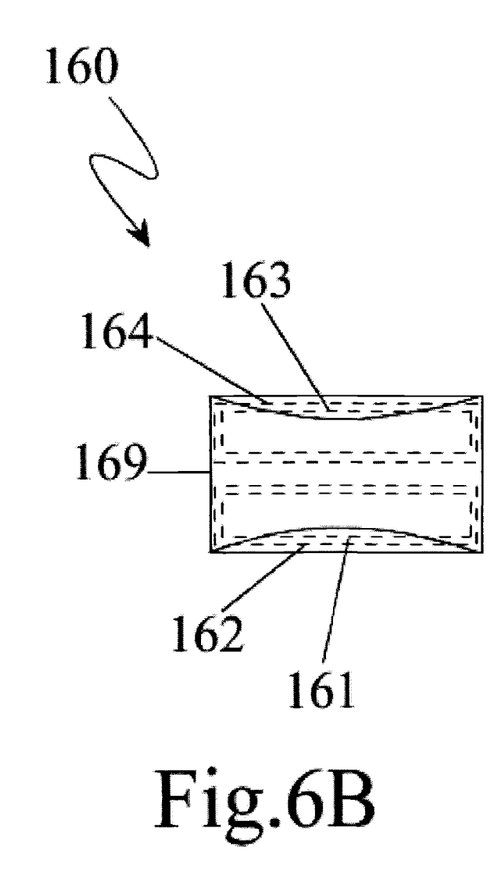
Figures 6C, 6D:
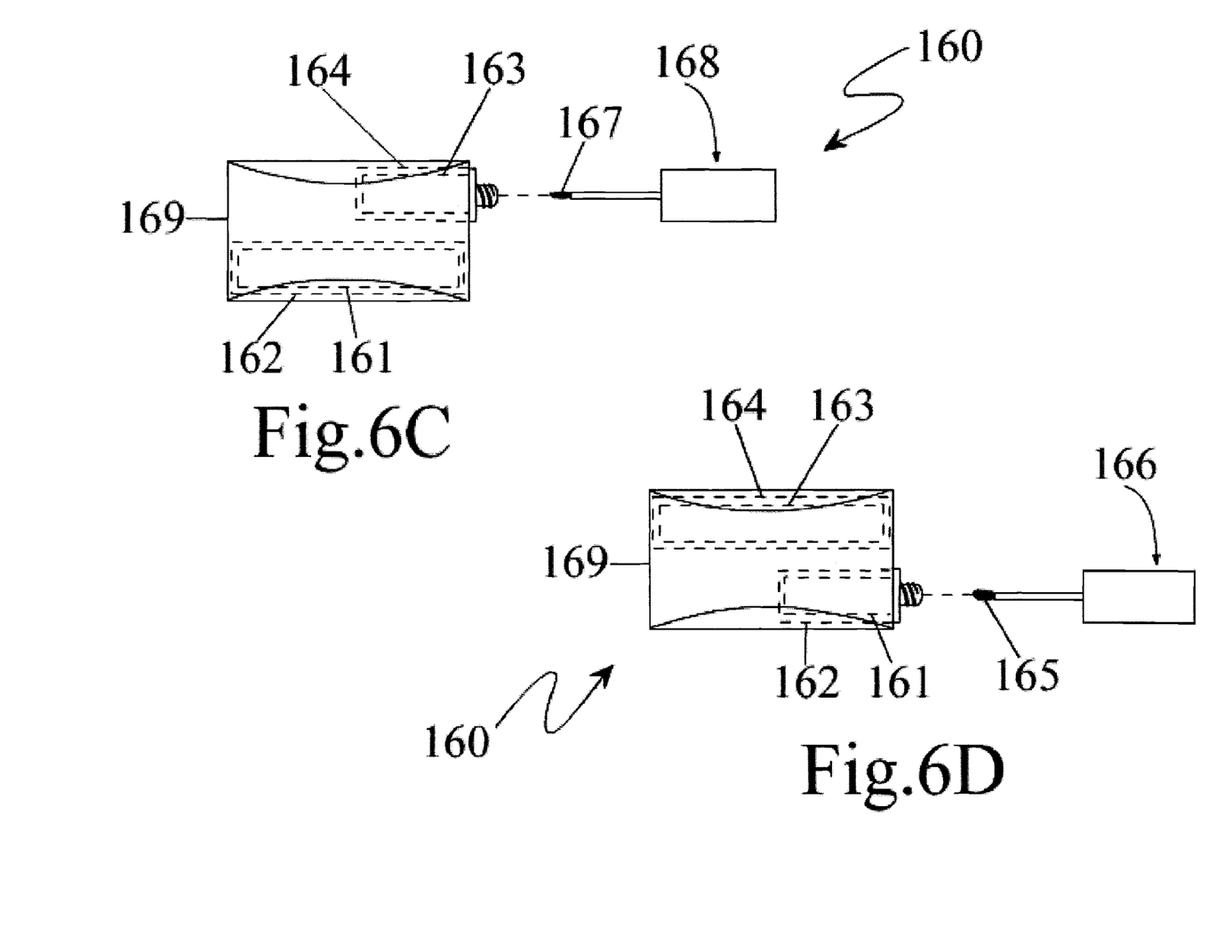

Another embodiment kit 160 is shown in FIGS. 6A to 6D. A kit 160 includes a first casing 162 and a second casing 164, both of which are installed in a frame or holder 169. The first casing 162 includes a reservoir 161, which holds an embodiment crème-to-powder formulation. The second casing 164 has a reservoir 163, which holds a sealant, preferably a liquid sealant. Each casing 162, 164 has a respective dispensing end that is removably closed or sealed by a respective wand 166, 168. The wands 166, 168 may, for example, screw onto the respective dispensing ends of their casings 162, 164. Each wand 166, 168 terminates in a respective applicator head 165, 167, that may be slid into its respective reservoir 161, 163. In preferred embodiments, the casings 162, 164 are slidably disposed within the frame 169. As shown in FIG. 6B, in a first configuration, such as when not in use, the first casing 162 and the second casing 164, together with the wands 166, 168, lie flush with the ends of the frame 169. As shown in FIG. 6C, in a second configuration, to apply the liquid sealant the user may push or slide the dispensing end of the second casing 164 from the frame 169 to expose the second wand 168, which may then be uncapped from the second casing 164 to apply the liquid sealant using the second applicator head 167. Similarly, as shown in FIG. 6D, in a third configuration, to apply an embodiment crème-to-powder formulation, the user may push or slide the dispensing end of the first casing 162 from the frame 169 to expose the first wand 166, which may then be uncapped from the first casing 162 to apply the crème-to-powder formulation using the first applicator head 165. The first applicator head 165 may be a brush 165 suitable for stippling the crème-to-powder formulation, while the second applicator head 167 may be a softer brush 167 suitable for contouring.

Figure 7:
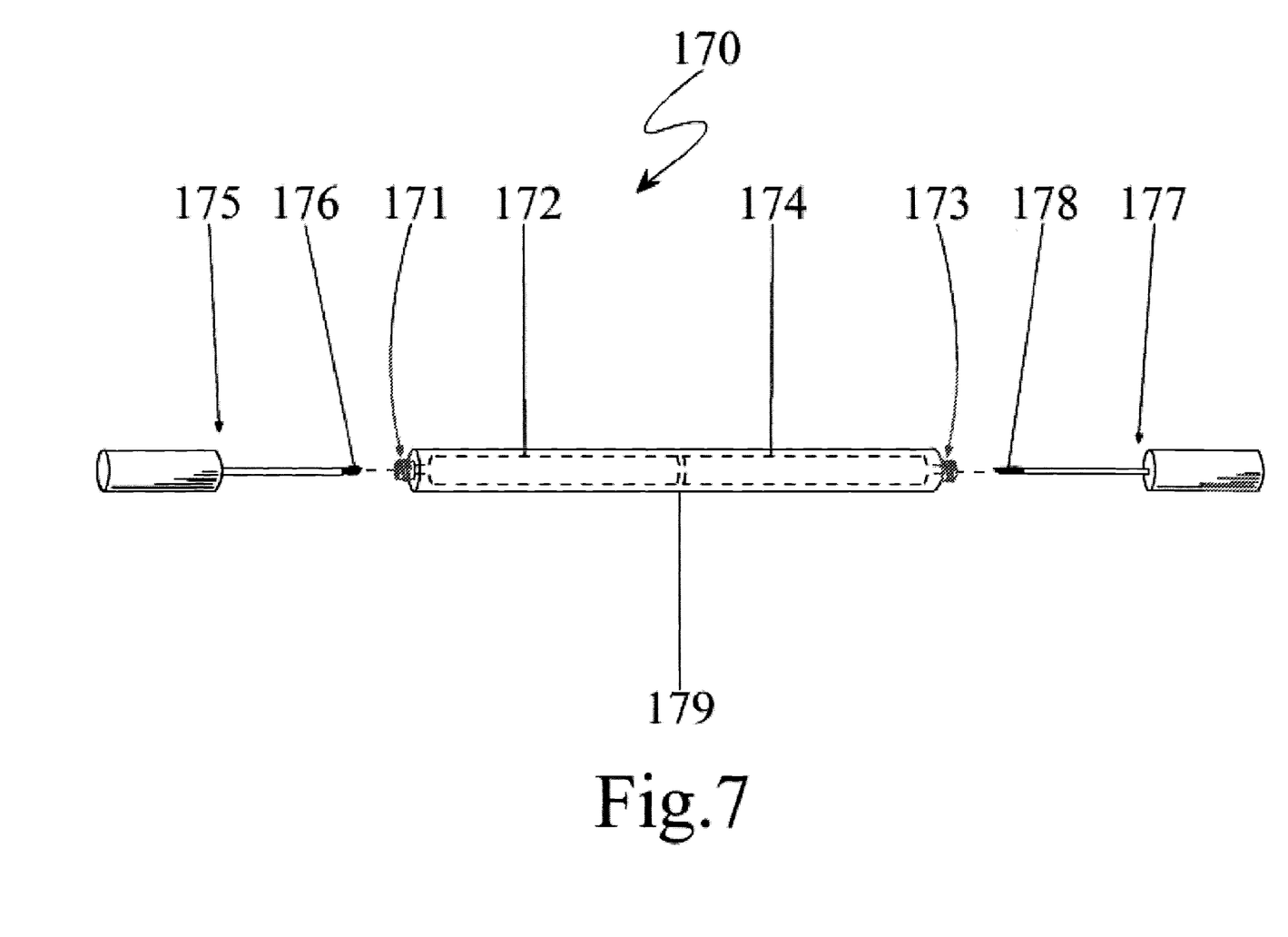
FIG. 7 shows a seventh system for an embodiment makeup application method.

Yet another embodiment kit 170 is shown in FIG. 7. The kit 170 includes a casing 179, which may be a tube or any other suitable shape, having a first reservoir 172 and a second reservoir 174. An embodiment crème-to-powder formulation is stored in the first reservoir 172, and a liquid sealant is stored in the second reservoir 174. The first reservoir 172 is fluidly connected to a first dispensing end 171 of the casing 179. Similarly, the second reservoir 174 is fluidly connected to a second dispensing end 173 of the casing 179. The casing 179 may be, for example, about 5½ inches long. A first wand 175 serves as a removable end cap to seal the first dispensing end 171, and a second wand 177 serves as a removable end cap to seal the second dispensing end 173. The first wand 175 terminates in a first applicator head 176, which in preferred embodiments is a firm, tufted brush, such as the first brush head 24 depicted in FIG. 1. The second wand 177 terminates in a second applicator head 178, which in preferred embodiments is also a brush that is softer than the first brush head 176, such as the second brush head 28 depicted in FIG. 1. A threaded connector or any other suitable mechanism may be used to removably connect the wands 175, 177 to their respective dispensing ends 171, 173. Preferably, each dispensing end 171, 173 is designed so that an aliquot of product from the respective reservoir 172, 174 is present on the applicator head 176, 178 when the wand 175, 177 is removed from the dispensing end 171, 173, such as by providing a narrow hole or the like for the dispensing ends 171, 173. As discussed earlier, and as applicable to the other embodiments, it will be appreciated that other types of applicators may be used instead of the brush heads 176, 178. For example, the wands 175, 177 could terminate in a sponge-like element, a mascara applicator, or any other device to permit application of the crème-to-powder formulation and liquid sealant to the eyebrows.

In alternative embodiments, the casing 179 may be designed so that the reservoirs 172, 174 are disposed parallel to each other, rather than serially to each other as shown in FIG. 7, similar to the embodiment 160 discussed above with reference to FIGS. 6A-6D. In such embodiments, the dispensing ends 171, 173 may be on the same side of the casing 179, or may be on opposite sides of the casing 179.

Figure 8:
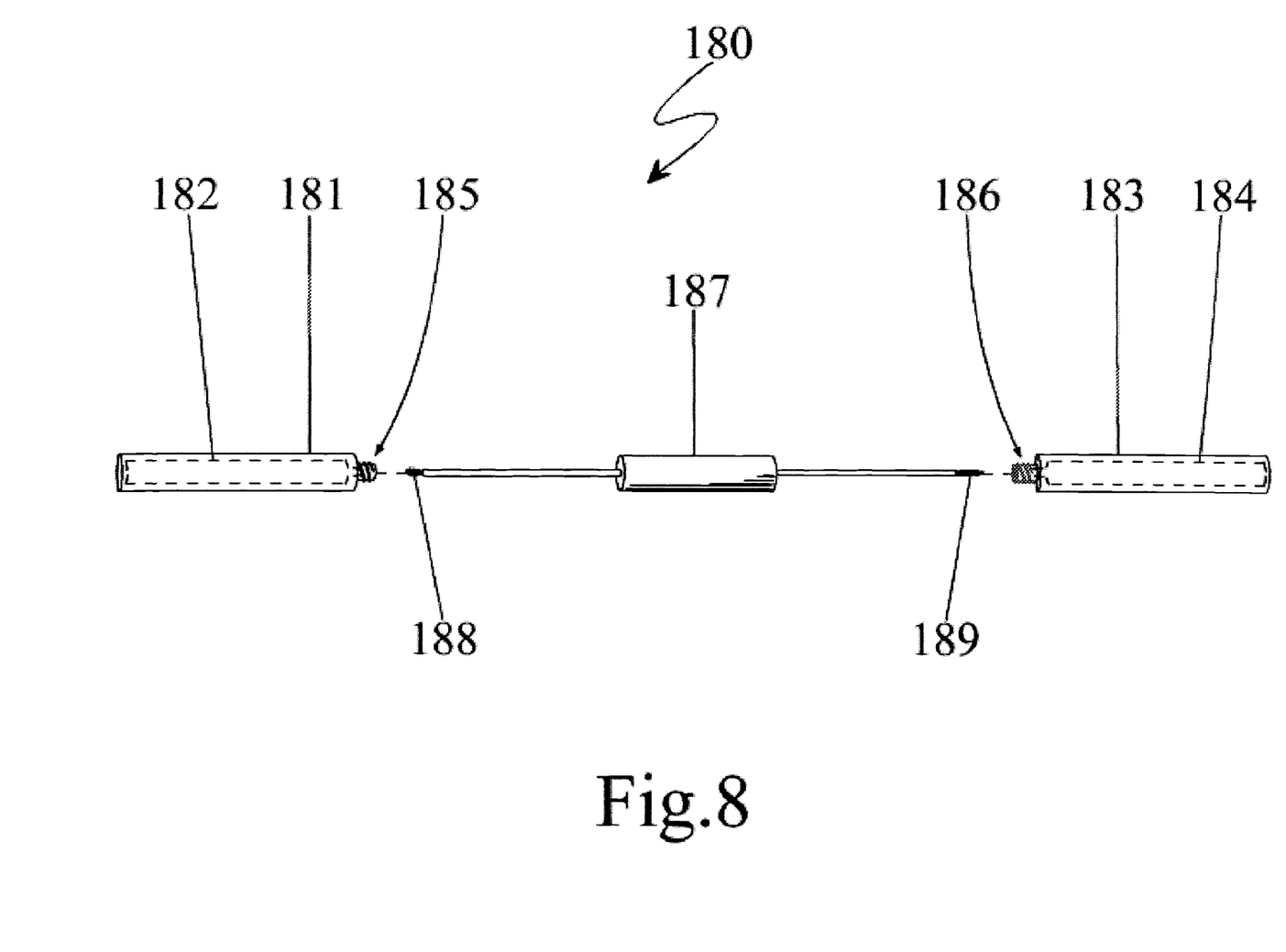
FIG. 8 shows an eighth system for an embodiment makeup application method.

Another variation of the kit 170 is shown in FIG. 8. A kit 180 includes a first casing 181 with a reservoir 182 for holding an embodiment crème-to-powder formulation, and a second casing 183 with a reservoir 184 for holding a liquid sealant. The reservoir 182 of the first casing 181 is fluidly connected to a dispensing end 185 of the first casing 181, and the reservoir 184 of the second casing 183 is fluidly connected to a dispensing end 186 of the second casing 183. A dual-headed wand 187 serves as a removable end cap to seal both of the dispensing ends 185, 186. Each end of the dual-headed wand 187 terminates in a respective applicator head 188, 189. In preferred embodiments, one of the applicator heads 188 is a firm, tufted brush, such as the first brush head 24 depicted in FIG. 1, and the other applicator head 189 is softer than the first brush head 188, such as the second brush head 28 depicted in FIG. 1. Threaded connectors or any other suitable mechanism may be used to removably connect each end of the dual-headed wand 187 to its respective dispensing end 185, 186. Preferably, each dispensing end 185, 186 is designed so that an aliquot of product from the respective reservoir 182, 184 is present on the applicator head 188, 189 when the applicator head 188, 189 is removed from the dispensing end 185, 186.

Figure 9:
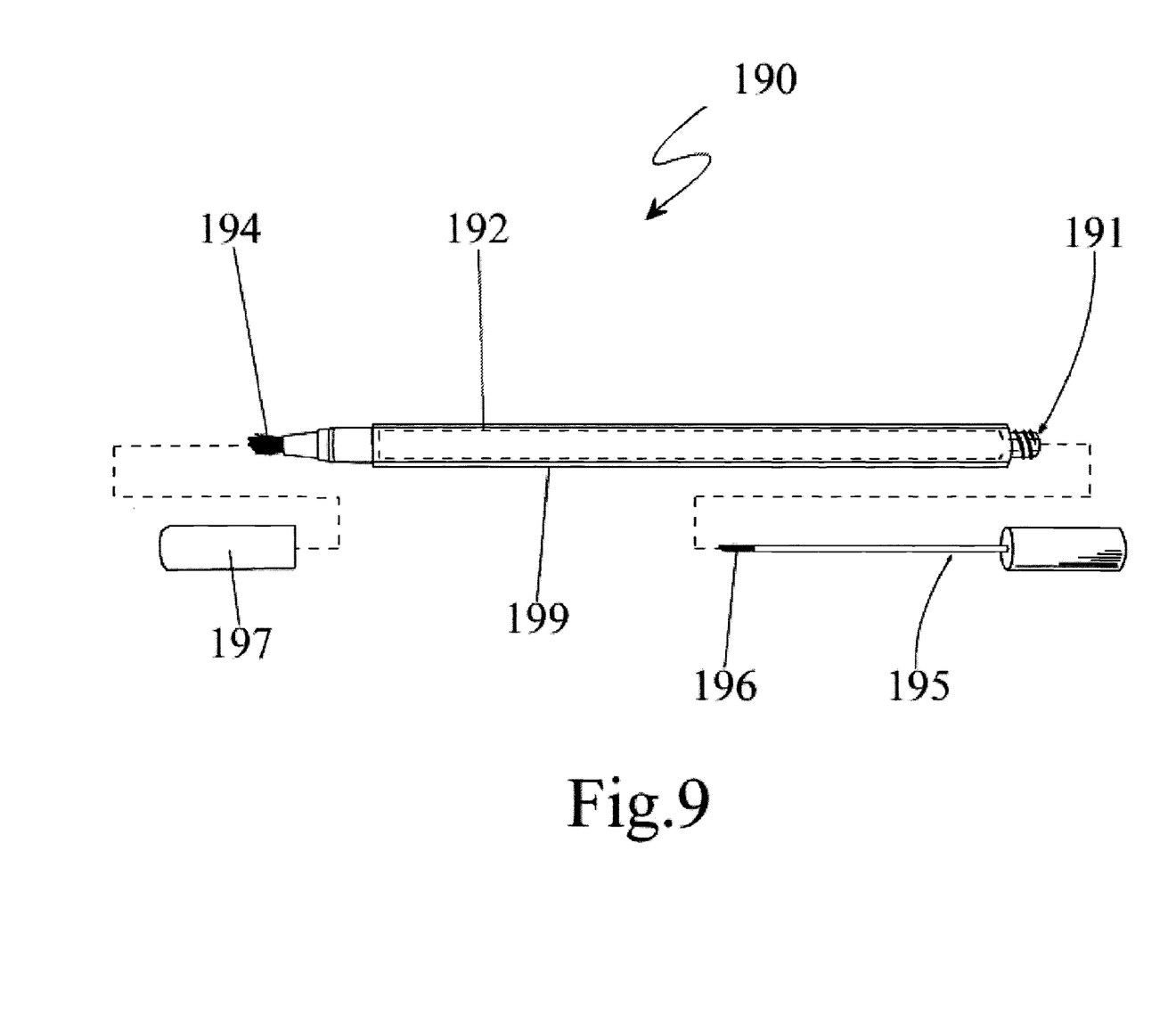
FIG. 9 shows a ninth system for an embodiment makeup application method.

Yet another embodiment eyebrow color applicator kit 190 is shown in FIG. 9. The applicator kit 190 includes a casing 199, which may be a tube or any other suitable shape, having a reservoir 192 and an applicator head 194, which is preferably a brush head similar, for example, to the first brush head 24 of FIG. 1. The brush head 194 may be covered by cap 197. An embodiment crème-to-powder formulation is stored in the reservoir 192. The reservoir 192 is fluidly connected to a dispensing end 191 of the casing 199, the dispensing end 191 being on an end of the casing 199 opposite to that of the applicator head 194. The casing 199 may be, for example, about 6½ inches long. A wand 195 serves as a removable end cap to seal the dispensing end 191. The wand 195 terminates in an applicator head 196, which may be a small sponge, foam wedge, brush or the like. A threaded connector or any other suitable mechanism may be used to removably connect the wand 195 to the dispensing end 191. Preferably, the dispensing end 191 is designed so that an aliquot of crème-to-powder formulation is present on the applicator head 196 when the wand 195 is removed from the dispensing end 191, such as by providing a narrow hole or the like. Utilizing the applicator head 196 of the wand 195, a user may apply the embodiment crème-to-powder formulation strategically, such as by dotting on, placing the formulation into the eyebrow hair or into sparse brow hair or onto bare skin. When placement of color as provided by the crème-to-powder formulation is done, the user can than put the 196 applicator back into the casing 199, and thus back into the reservoir 192, simultaneously sealing the dispensing end 191. The user may then expose the second applicator 194, i.e., the brush 194, to stipple the crème-to-powder formulation placed by the first applicator head 196.

In yet other embodiments, a bottle of liquid sealant may be provided with the applicator 190, such as the bottle 150 shown in FIG. 5. The sealant may then applied over the eyebrows, sparse brows or the bare skin of the brow to seal the color as provided by the crème-to-powder formulation, rendering this color sweat-proof and smudge-proof.

Figure 10:
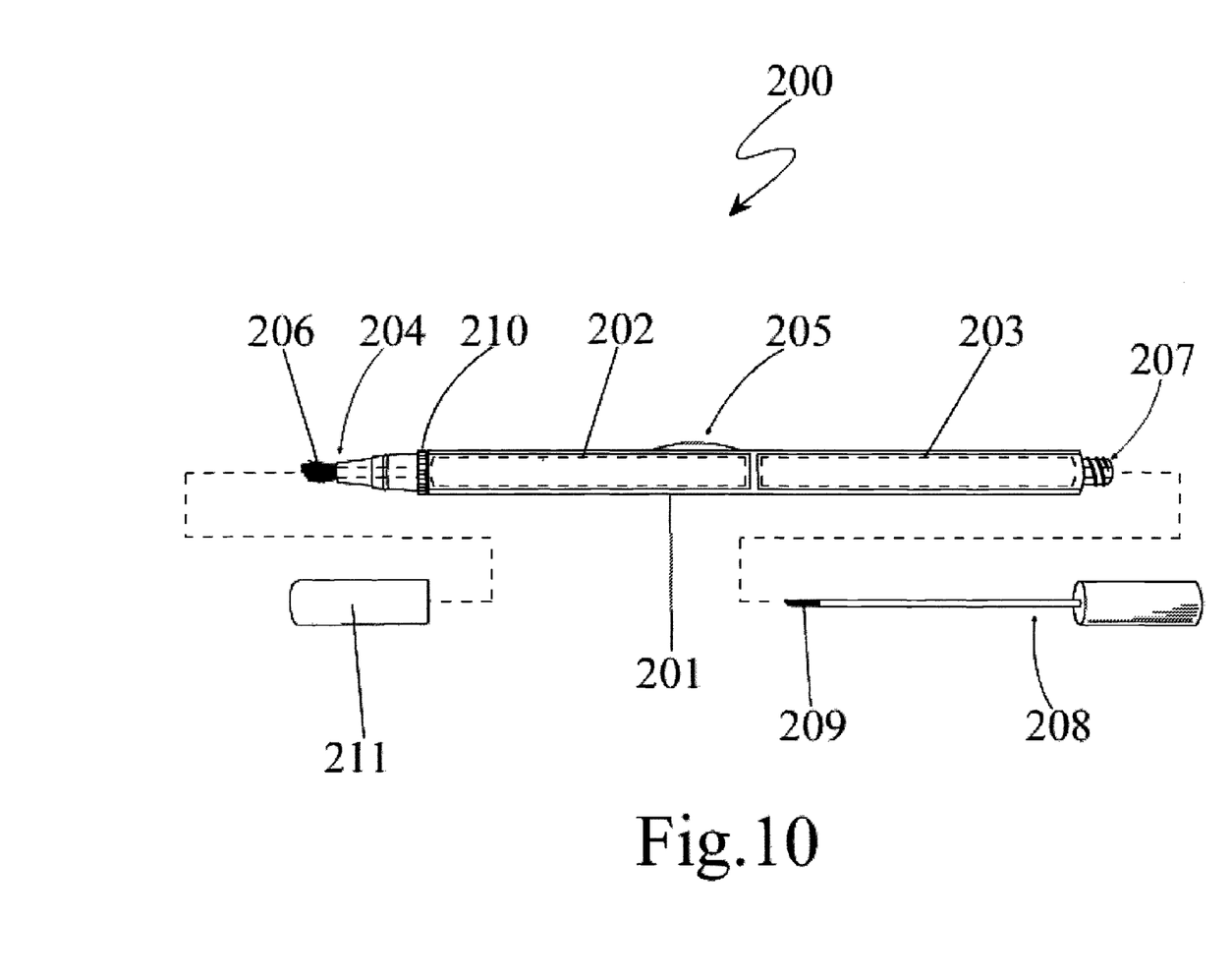
FIG. 10 shows a tenth system for an embodiment makeup application method.

Yet another embodiment kit 200 if shown in FIG. 10. The kit 200 includes a casing 201 with a first reservoir 202 and a second reservoir 203. The first reservoir 202 is used to hold an embodiment crème-to-powder formulation, and the second reservoir 203 holds a liquid sealant. The first reservoir 202 is fluidly connected to a first dispensing end 204, which terminates in a first applicator head 206. The first applicator head 206 is thus fluidly connected to the first dispensing end 204. Any suitable dispensing system, which may employ, for example a button 205, a dial 210, or the like, may be employed to permit a user to dispense aliquots of the crème-to-powder formulation held in the first reservoir 202 from the first dispensing end 204 and onto the first applicator head 206. The second reservoir 203 is fluidly connected to a second dispensing end 207. The second dispensing end 207 accepts, and is sealed by, a wand 208. The wand 208 terminates in a second applicator head 209, and is used to apply aliquots of the liquid sealant held in the second reservoir 203 onto the eyebrows of a user.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for applying eyebrow makeup comprising, while in a crème state, applying a crème-to-powder formulation to an eyebrow, or to skin at a location corresponding to an eyebrow, wherein the crème-to-powder formulation has a matte color adapted for application as eyebrow makeup and a viscosity from 1,000 centipoise to 10,000,000 centipoise.

2. The method of claim 1 further comprising applying a sealant over the crème-to-powder formulation.

3. The method of claim 1 wherein the sealant is a liquid sealant.

4. The method of claim 1 wherein the crème-to-powder formulation comprises a crème-to-powder base and at least a pigment to provide the crème-to-powder formulation a color suitable for application as eyebrow makeup.

5. The method of claim 1 wherein the crème-to-powder formulation is applied only to the eyebrow, or to skin at a location corresponding to an eyebrow.

6. The method of claim 1 wherein the crème-to-powder formulation has a color selected from the set consisting of the colors defined by the following Pantone® matching system (PMS) color values: 134, 1345, 138, 1385, 139, 1395, 140, 1405, 145, 148, 153, 1535, 154, 1545, 155, 160, 1605, 161, 1615, 1817, 400, 401, 402, 403, 404, 405, 406, 407, 408, 409, 410, 411, 412, 420, 421, 422, 423, 424, 425, 426, 451, 452, 490, 712, 713, 714, 715, 716, 717, 718, 719, 720, 721, 722, 723, 724, 725, 726, 727, 728, 729, 730, 731, and 732.

7. The method of claim 6 wherein the crème-to-powder formulation has a color selected from the set consisting of the following PMS color values: 1345, 1355, 1385, 1395, 140, 1405, 146, 153, 154, 160, 400, 401, 402, 406, 1817, 420, 422, 451, 452, 490, 712, 719, 721, 727, 729, and 732.

8. A kit comprising:
a first casing comprising a first reservoir and a first dispensing end fluidly connected to the first reservoir;
a crème-to-powder formulation disposed in the first reservoir, the crème-to-powder formulation having a matte color adapted for application as eyebrow makeup and a viscosity from 1,000 centipoise to 10,000,000 centipoise; and
a first applicator head for applying the crème-to-powder formulation to an eyebrow or to skin at a location corresponding to an eyebrow.

9. The kit of claim 8 wherein the first applicator head is attached to an end of the casing, and the kit further comprises a wand for removably closing the first dispensing end, the wand comprising a second applicator head.

10. The kit of claim 8 wherein the casing further comprises a second reservoir, a second dispensing end fluidly connected to the second reservoir, and a liquid sealant is disposed within the second reservoir.

11. The kit of claim 10 further comprising a first dispensing system for dispensing an aliquot of the crème-to-powder formulation from the first reservoir to the first dispensing end in response to user activation of the first dispensing system, a second dispensing system for dispensing an aliquot of the liquid sealant from the second reservoir to the second dispensing end in response to user activation of the second dispensing system, a second applicator head fluidly connected to the second dispensing end, and wherein the first applicator head is fluidly connected to the first dispensing end.

12. The kit of claim 10 further comprising a first dispensing system for dispensing an aliquot of the crème-to-powder formulation from the first reservoir to the first dispensing end in response to user activation of the first dispensing system, a wand for removably closing the second dispensing end, the wand comprising a second applicator head, and wherein the first applicator head is fluidly connected to the first dispensing end.

13. The kit of claim 10 further comprising a first wand for removably closing the first dispensing end, the first applicator head attached to the first wand, and a second wand for removably closing the second dispensing end, the second wand comprising a second applicator head.

14. The kit of claim 8 wherein the first casing further comprises a first dispensing system for dispensing the crème-to-powder formulation from the first reservoir to the first dispensing end.

15. The kit of claim 14 further comprising a second casing, the second casing comprising a second dispensing end and a second reservoir fluidly connected to the second dispensing end, and a liquid sealant is disposed in the second reservoir.

16. The kit of claim 15 further comprising a wand comprising a second applicator head for removable closing the second dispensing end, and the first applicator head is fluidly connected to the first dispensing end.

17. The kit of claim 15 wherein the second casing further comprises a second dispensing system for dispensing the liquid sealant from the second reservoir to the second dispensing end.

18. The kit of claim 8 further comprising a second casing, the second casing comprising a second reservoir and a second dispensing end fluidly connected to the second reservoir, and a liquid sealant is disposed in the second casing.

19. The kit of claim 18 further comprising a dual-ended wand for removably closing the first dispensing end and the second dispensing end, the first applicator head connected to one end of the dual-ended wand, a second applicator head connected to another end of the dual-ended wand.

\* \* \* \* \*